United States Patent
Goethel

(10) Patent No.: US 9,778,204 B2
(45) Date of Patent: Oct. 3, 2017

(54) APPARATUS AND METHOD FOR IDENTIFYING FOREIGN BODIES IN AN INDUCTIVE CHARGING SYSTEM

(71) Applicant: Bayerische Motoren Werke Aktiengesellschaft, Munich (DE)

(72) Inventor: Joachim Goethel, Munich (DE)

(73) Assignee: Bayerische Motoren Werke Aktiengesellschaft, Munich (DE)

(*) Notice: Subject to any disclaimer, the term of this patent is extended or adjusted under 35 U.S.C. 154(b) by 292 days.

(21) Appl. No.: 14/633,214

(22) Filed: Feb. 27, 2015

(65) Prior Publication Data
US 2015/0168309 A1   Jun. 18, 2015

Related U.S. Application Data

(63) Continuation of application No. PCT/EP2013/067900, filed on Aug. 29, 2013.

(30) Foreign Application Priority Data

Aug. 30, 2012   (DE) .................. 10 2012 215 376

(51) Int. Cl.
*H02J 7/00*   (2006.01)
*G01N 21/88*   (2006.01)
*B60L 11/18*   (2006.01)

(52) U.S. Cl.
CPC ........ *G01N 21/8851* (2013.01); *B60L 11/182* (2013.01); *B60L 11/1829* (2013.01);
(Continued)

(58) Field of Classification Search
CPC ............... B60L 11/182; B60L 11/1829; B60L 11/1833; G01N 21/8851
(Continued)

(56) References Cited

U.S. PATENT DOCUMENTS

2011/0074346 A1   3/2011   Hall et al.
2012/0187757 A1*   7/2012   Wechlin ............... B60L 11/182
                                                                              307/9.1
(Continued)

FOREIGN PATENT DOCUMENTS

| DE | 20 2009 009 689 U1 | 12/2010 |
|---|---|---|
| DE | 10 2009 033 236 A1 | 1/2011 |
| DE | 10 2010 026 780 A1 | 1/2012 |
| DE | 10 2011 076 186 A1 | 11/2012 |
| DE | 10 2011 109 834 A1 | 2/2013 |
| GB | 2 347 801 A | 9/2000 |
| WO | WO 2011/112795 A1 | 9/2011 |
| WO | WO 2012/047779 A1 | 4/2012 |

OTHER PUBLICATIONS

German Search Report dated Apr. 9, 2013 with partial English-language translation (Nine (9) pages).
(Continued)

*Primary Examiner* — Edward Tso
*Assistant Examiner* — Aaron Piggush
(74) *Attorney, Agent, or Firm* — Crowell & Moring LLP

(57) ABSTRACT

An apparatus and method for identifying foreign objects in an inductive charging system having a charging unit and a vehicle for inductive charging, in which the charging unit includes a primary coil and the vehicle has a secondary coil in order to transmit electrical power from the primary coil to the secondary coil during a charging operation. The vehicle includes a camera system, and a camera control unit. The camera system captures at least one image of the charging unit when the vehicle approaches the charging unit, at the beginning of a charging operation and/or during a charging operation. The camera control unit digitally processes the at least one captured image in order to detect a foreign body located on the charging unit.

20 Claims, 1 Drawing Sheet

(52) U.S. Cl.
CPC ....... *B60L 11/1833* (2013.01); *B60L 11/1835* (2013.01); *B60L 2230/16* (2013.01); *B60L 2250/10* (2013.01); *G01N 2201/12* (2013.01); *Y02T 10/7005* (2013.01); *Y02T 10/7088* (2013.01); *Y02T 90/121* (2013.01); *Y02T 90/122* (2013.01); *Y02T 90/125* (2013.01); *Y02T 90/128* (2013.01); *Y02T 90/14* (2013.01); *Y02T 90/163* (2013.01)

(58) Field of Classification Search
USPC .......................................... 320/104, 108, 109
See application file for complete search history.

(56) References Cited

U.S. PATENT DOCUMENTS

| | | | |
|---|---|---|---|
| 2012/0200151 A1* | 8/2012 | Obayashi | B60L 11/123 307/9.1 |
| 2013/0114640 A1 | 5/2013 | Elias et al. | |
| 2014/0111155 A1 | 4/2014 | Bendicks | |

OTHER PUBLICATIONS

International Search Report (PCT/ISA/210) dated Mar. 3, 2014 with English-language translation (Six (6) pages).

* cited by examiner

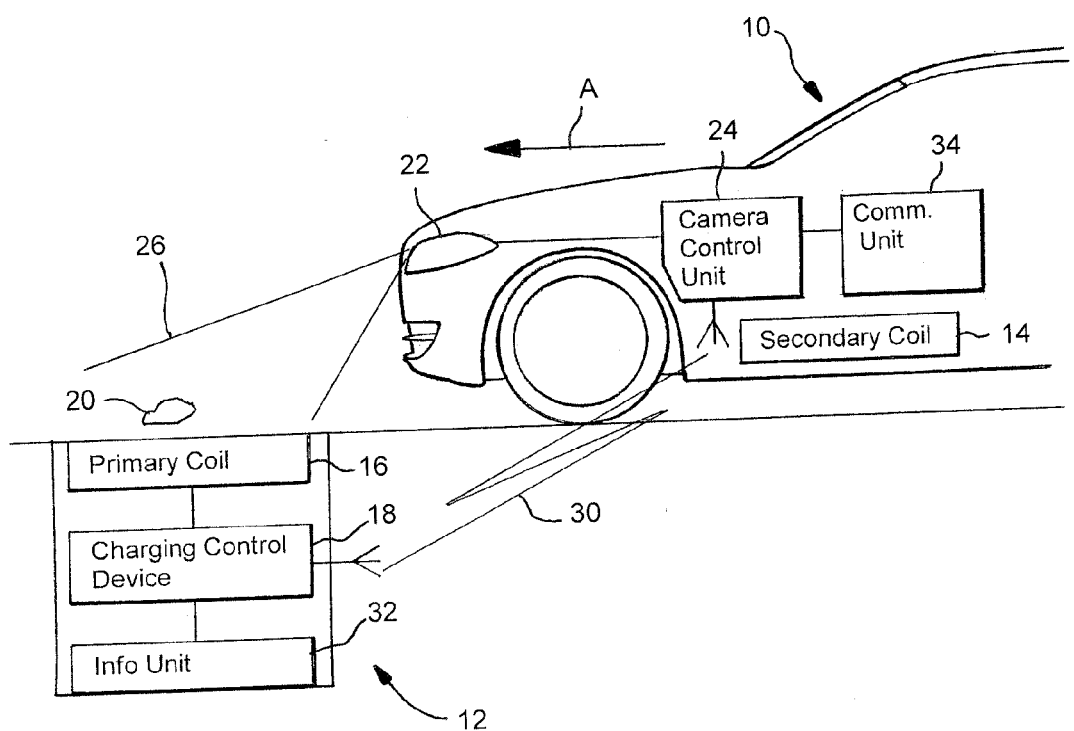

APPARATUS AND METHOD FOR IDENTIFYING FOREIGN BODIES IN AN INDUCTIVE CHARGING SYSTEM

CROSS REFERENCE TO RELATED APPLICATIONS

This application is a continuation of PCT International Application No. PCT/EP2013/067900, filed Aug. 29, 2013, which claims priority under 35 U.S.C. §119 from German Patent Application No. 10 2012 215 376.4, filed Aug. 30, 2012, the entire disclosures of which are herein expressly incorporated by reference.

BACKGROUND AND SUMMARY OF THE INVENTION

The invention relates to an apparatus and method for identifying foreign objects in an inductive charging system having a charging unit and having a vehicle for inductive charging, in which the charging unit includes a primary coil, and the vehicle includes a secondary coil in order to transmit electrical power from the primary coil to the secondary coil during a charging operation.

Electric and hybrid vehicles can usually be charged with an external charging unit by use of a cable connection. Charging without a cable, which can be implemented by inductive charging methods, is more convenient. Inductive transmission systems are known from the prior art, see for example GB 2 347 801 A1. The induction charging apparatus consists of a charging unit external to the vehicle having a primary coil and a vehicle unit having a secondary coil. With inductive charging, the two coils are spatially opposite one another and form a transmission region in which the electromagnetic transmission field is substantially located.

In addition, modern electric and hybrid vehicles have various types of driver assistance systems. These are complex electronic systems which support the vehicle user when operating the vehicle. Camera-based parking aids or lane guidance aids are cited as an example.

It is an object of the invention to provide an improved apparatus having a charging unit and having a vehicle for inductive charging.

According to the invention, the vehicle includes a camera system and a camera control unit. The camera system captures at least one image of the charging unit when approaching a charging station, at the beginning of a charging operation and/or during a charging operation. The camera control unit digitally processes the at least one captured image in order to detect a foreign body located on the charging unit.

Here, a charging operation is understood to be particularly the time period during which a transmission of electrical power takes place from the charging unit to the vehicle.

The term "approaching a charging station" encompasses an operation in which the vehicle assumes a specific parking position in spatial relationship to the charging unit in order to carry out a charging operation. This can also be supported by driver assistance systems such as a parking aid.

Without restricting generality, objects of all kinds, in particular however metallic objects, which are located in the transmission region during a charging operation, are described as foreign bodies. If an object comes to lie e.g. on the charging unit, which means that this object is also located in the transmission region, then this object can be detected by the captured image. The camera control unit determines the existence of a foreign body in the transmission region using digital image processing techniques based on the captured image.

According to a preferred embodiment of the invention, the charging unit includes a charging control device which controls the primary coil. At least one unidirectional data connection can be established from the camera control unit to the charging control device.

It is advantageous if the camera control unit generates a detection signal when a foreign body is detected, and the detection signal can be transmitted from the camera control unit to the charging control device by way of the established data connection.

When the detection signal is received from the camera control unit, the charging control device interrupts or reduces the transmission of power from the primary coil to the secondary coil.

This means that when a foreign body is detected, the apparatus suppresses or reduces the transmitted power so that the foreign body is subjected to a weakened transmission field or is no longer subjected to a transmission field. For this purpose, the charging control device receives the detection signal of the camera control unit and, as the driver of the primary coil, suppresses the transmission field located in the transmission region which emanates from the primary coil or reduces its field strength.

According to a preferred embodiment of the invention, the vehicle includes a communications unit to which the detection signal from the camera control unit can be transmitted and, when the detection signal is received by the communications unit, the communications unit outputs a discernible warning signal.

In this way, attention is drawn to the detected foreign body, for example, in a discernible manner for the vehicle user. This can, for example, be a visual display in the region of the driver's compartment or a discernible acoustic signal outside the vehicle. The discernible output can also contain a handling instruction, such as a request to clean the charging unit.

In order to detect a foreign body, a reference image of the charging unit without a foreign body on the charging unit or a foreign body in the transmission region is stored in the camera control unit. The camera control unit compares the at least one captured image with the reference image, wherein the deviation of the captured image from the reference image means the detection of a foreign body.

The detection of a foreign body is therefore based on a comparison of a captured actual image with the stored reference image. Preferably, the camera control unit carries out the image comparison using a segmenting method or using a pattern recognition method.

According to a further variant of the invention, the camera system and the camera control unit are components of a driver assistance system of the vehicle.

The invention is based on the considerations presented below.

Methods are known for electric vehicles which enable contactless, preferably inductive, charging of the motor vehicle on-board electrical system or of the storage device(s) contained therein.

As with inductive charging, the transmission of energy can be disrupted by metallic or electrically conducting materials between the two sides of the contactless transmission, measures must therefore be taken to detect such objects or materials and ensure countermeasures such as an interruption of the energy transmission. This successfully avoids undesirable heating of the foreign body and possible negative consequences.

The monitoring methods known from the prior art are either inadequate, as an overheating of very small or thin-walled conductive materials, such as a small coin for example, is not detected reliably or not quickly enough. However, the elimination of any potential hazard due to overheating of foreign bodies has the highest priority. Monitoring methods have a high degree of complexity without synergies with the technical monitoring systems (e.g. driver assistance systems) present in the vehicle being usable. Such solutions are therefore cost and space-intensive, as additional hardware is required.

A measure to use driver assistance systems of a vehicle during inductive charging to identify foreign bodies is provided.

For example, a sensor for image processing techniques, (e.g. an optical sensor such as a mono camera or stereo camera) integrated within a driver assistance system can be used to detect foreign bodies during inductive charging. This means that when the object to be charged, that is to say the vehicle, approaches a primary coil, that is to say the energy source, the existing sensor is activated or becomes activated. Where appropriate, the activation takes place automatically when approaching within a spatial boundary or, alternatively, a function takes place by manual activation. This sensor has image processing capabilities and compares every captured actual image with a reference image stored in the vehicle. The reference image specifies how the primary unit without any foreign body must be characterized. If the actual image deviates from the reference image, it is concluded that contamination or a foreign body is located in the region of the primary coil and inductive charging is prevented and/or the user of the system is given an appropriate hazard warning with a corresponding handling recommendation (e.g. request to clean). The imaging method can also preferably be carried out stereoscopically or spatially in order to detect size, type and degree of risk of the contamination or of the foreign body.

Other objects, advantages and novel features of the present invention will become apparent from the following detailed description of one or more preferred embodiments when considered in conjunction with the accompanying drawings.

BRIEF DESCRIPTION OF THE DRAWING

FIG. 1 is a schematic diagram illustrating an embodiment of the invention.

DETAILED DESCRIPTION OF THE DRAWING

Referring to FIG. 1, when a vehicle 10 is charged inductively, electrical power is transmitted without a cable to the vehicle from a charging unit 12 external to the vehicle. The energy transmitted in a certain time is used, for example, to bring an electrochemical energy storage device of the vehicle to a higher state of charge.

For charging, the vehicle has, in particular, a secondary coil 14. The charging unit 12 substantially comprises a primary coil 16 which generates an alternating electromagnetic field which induces a voltage in the secondary coil 14 using the principle of induction. This induced voltage can be used in the vehicle as a charging voltage. The alternating electromagnetic field is hereinafter referred to as the transmission field. The primary coil 16 is driven by a charging control device 18 which is included in the charging unit 12.

When the apparatus is used for inductively charging a vehicle energy storage device, the secondary coil 14 can be integrated in the region of the vehicle floor. The charging unit 12 is located outside the vehicle and, for example, can be integrated in a vehicle parking place and/or vehicle charging station.

The power transmission between the charging unit 12 and the vehicle 10 is particularly efficient when the vehicle assumes a charging position. This means that the vehicle is localized in the region of the vehicle charging station such that there is good spatial coverage of the secondary coil by the primary coil with regard to the x-direction and the y-direction. The x-direction and the y-direction relate to the vehicle coordinate system known to the person skilled in the art with the x-axis along the vehicle longitudinal axis, the y-axis along the vehicle transverse axis and the z-axis as the vehicle vertical axis. In the charging position, the field region of the transmission field, which is located between the primary coil and the secondary coil during charging, is referred to as the transmission region. Without restricting generality, the primary coil substantially has an extension along the x-y plane of the vehicle-related coordinate system. Alternatively, this can also be the case along the y-z plane for example.

If, during a charging operation, an object 20 which interacts with the transmission field, e.g. a piece of metal, is located in the transmission region and comes to lie on the vehicle charging station or vehicle parking place in the region of the charging unit, in particular in the region of the primary coil of the charging unit, this results in a local change in the transmission field in the region of the piece of metal and in regions adjacent to the piece of metal. Due to the skin effect, eddy currents in the metallic object displace the transmission field from its interior. These eddy currents cause heating of the piece of metal. This is not desirable for safety reasons and is a condition to be avoided. The transmission region must therefore be monitored with regard to objects, hereinafter referred to as foreign bodies, located in the transmission region.

For monitoring purposes, it is assumed that the vehicle has driver assistance systems. In particular, the vehicle has camera-based driver assistance systems, e.g. an all-round camera system which includes at least one imaging camera 22.

A camera control unit 24 is associated with the driver assistance camera system. The camera system includes at least one camera. The camera system is optionally equipped with additional cameras for monitoring the transmission region. Each camera is characterized by an image capturing region 26 (imaging field).

On approaching the charging position (arrow A) and when the charging position has been reached, the transmission region between the primary coil and the secondary coil (or at least the primary coil or a housing of the primary coil) lies fully in the image capturing region of at least one camera of the camera system. According to an alternative embodiment, the transmission region lies only partially in the respective image capturing regions of the cameras of the camera system, wherein, however, together, the image capturing regions of at least two cameras of the camera system fully capture the transmission region (or at least the primary coil or a housing of the primary coil).

Common to all embodiments is that for at least one moment in time during the approach phase to the charging position or when the charging position has been reached, i.e.

immediately before the start of the charging operation and/or during a charging operation, the entire transmission region (or at least the primary coil or at least a housing of the primary coil) lies within the field of view of the camera system by way of one or more cameras.

The camera system can capture an image of this image field. This image is hereinafter referred to as the charging image. According to the embodiments described, one camera or a plurality of cameras are involved in capturing the charging image. In the case of a plurality of cameras, the charging image is formed jointly from partial images, wherein the number of partial images is equal to the number of the plurality of cameras.

The charging image is generated in the camera control unit or is generated by the camera system and transmitted to the camera control unit. In the camera control unit, the charging image is used as an object for one or more digital image processing methods which can be carried out by the camera control device.

If the camera system includes a plurality of cameras, these can be located in different available spaces of the vehicle. The camera system and the camera control unit form an image capturing unit, which also has means for data transmission between the cameras and the camera control unit. Alternatively, the camera system and the camera control unit can be integrated in a single unit or housing. Optionally, the at least one camera of the camera system can be designed as a light sensor array.

The task of the digital image processing system is to detect a foreign body in the transmission region. For this purpose, a comparison image is stored in the camera control unit. The comparison image corresponds to the charging image with regard to the field of view. The comparison image shows no foreign bodies in the transmission region. The image processing consists substantially of a comparison of the charging image with the comparison image. For this purpose, the comparison image is subtracted from the charging image. The result of the subtraction shows the foreign body. Optionally, image correction techniques and image reprocessing techniques which compensate for brightness differences, which are known to the person skilled in the art, are used before the subtraction in order, for example, to be able to keep the result of the subtraction free from shadows in the charging image and comparison image, or free from image capturing errors. The subtraction result is hereinafter referred to as the subtraction image.

The subtraction image is, in turn, analyzed for contrast differences using a pixel-by-pixel or segment-by-segment threshold method, which is also known to the person skilled in the art. If the subtraction image has specifiable contrast differences which can be stored in the camera control unit or if these contrast differences in the subtraction image are exceeded, this is equivalent to the detection of a foreign body and the camera control unit generates a detection signal.

Alternatively, the segmentation method can be used on the subtraction image. In this case, an edge-oriented method which searches for edges in the subtraction image is sufficient. The detection of edges results in the generation of the detection signal.

Alternatively or additionally, a pattern recognition algorithm is carried out on the charging image. The primary coil, for example, or the housing which encompasses the primary coil, is preferably used here as a stored object. If a foreign body is located in the transmission region, the deviation from the stored object which is caused thereby leads to the stored object being undetectable by the algorithm. It can therefore be concluded that a foreign body is present, which results in the generation of the detection signal.

The charging image is captured before the start of a charging operation and/or during the charging operation. According to a further embodiment, captures are repeatedly made when approaching the charging position, i.e. when assuming the charging position, before the start of a charging operation and during the charging operation, and the charging image is thereby refreshed. In doing so, the time between refreshing the charging image is at least equal to the time necessary for processing the charging image. In this way, the transmission region is continuously monitored while approaching the charging position and during a charging operation, so that, by way of example, an object, such as a rolling coin for example, entering the transmission region during a charging operation can also be detected.

The detection signal is preferably transmitted by the camera control unit to the charging control device. For this purpose, a direct wireless connection 30 can be established between the camera control unit 24 and the charging control device 18, or a wireless connection between other components of the vehicle or the charging unit can be used to transmit the detection signal output by the camera control unit to the charging control device.

If the detection signal is received by the charging control device as the vehicle approaches the charging position, the charging control device suppresses inductive charging. i.e., a charging operation is not initiated or started. If the detection signal is received by the charging control device during a charging operation which has already been initiated, the charging control device interrupts the charging operation, the generation of the electromagnetic field by the primary coil, or reduces the field strength of the field.

In addition, a discernible warning signal, e.g. an acoustic signal, can be output at the charging unit by means of a suitable output unit 32 of the charging unit 12, e.g. by means of a loudspeaker.

According to a further embodiment, the detection signal can be transmitted by the camera control unit 24 to a man-machine interface 34 in the vehicle. After receiving the detection signal, the man-machine interface outputs a discernible warning signal or handling instruction. The handling instruction can, for example, be an instruction to remove a foreign body from the transmission region.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An apparatus for identifying a foreign body in an inductive charging system, the inductive charging system comprising a charging unit having a primary coil and a vehicle having a secondary coil, wherein electrical power is transmitted from the primary coil to the secondary coil during a charging operation, the apparatus comprising:
   a camera system of the vehicle; and
   a camera control unit coupled to the camera system, wherein
   the camera system is configured to capture at least one image of the charging unit as the vehicle approaches the charging unit and before the vehicle reaches a charging position of the charging operation, and the camera control unit digitally processes the at least one captured image in order to detect the foreign body located on the charging unit.

2. The apparatus according to claim 1, wherein:
the charging unit comprises a charging control device,
the primary coil of the charging unit is controllable by the charging control device, and
at least one unidirectional data connection is establishable from the camera control unit to the charging control device.

3. The apparatus according to claim 2, wherein:
the camera control unit generates a detection signal when a foreign body is detected, and
the detection signal is transmitted from the camera control unit to the charging control device via the established data connection.

4. The apparatus according to claim 3, wherein when the detection signal is received by the charging control device, the charging control device suppresses, interrupts or reduces power transmission from the primary coil to the secondary coil.

5. The apparatus according to claim 4, wherein:
the charging unit further comprises an information unit; and
when the detection signal is received by the charging control device, the information unit outputs a warning signal.

6. The apparatus according to claim 3, wherein:
the charging unit further comprises an information unit; and
when the detection signal is received by the charging control device, the information unit outputs a warning signal.

7. The apparatus according to claim 3, wherein
the vehicle includes a communications unit,
the detection signal is transmitted from the camera control unit to the communications unit, and
when the detection signal is received by the communications unit, the communications unit outputs a warning signal.

8. The apparatus according to claim 1, wherein:
a referenced image of the charging unit without a foreign body on the charging unit is stored in the camera control unit,
the camera control unit compares the at least one captured image with the referenced image, and
a deviation of the captured image from the referenced image identifies a detection of a foreign body.

9. The apparatus according to claim 8, wherein the camera control unit carries out the image comparison using a segmenting method or a pattern recognition method.

10. The apparatus according to claim 1, wherein the camera system and the camera control unit also function as a driver assistant system of the vehicle.

11. The apparatus according to claim 1, wherein the camera system is further configured to capture at least one image of the charging unit when the vehicle is in the charging position at a beginning of the charging operation.

12. The apparatus according to claim 11, wherein the camera system is further configured to capture at least one image of the charging unit when the vehicle is in the charging position during the charging operation.

13. A method of identifying a foreign body in an inductive charging system comprising a charging unit having a primary coil and a vehicle having a secondary coil, electrical power being inductively transmitted from the primary coil to the secondary coil during a charging operation, the method comprising the acts of:
obtaining, via a camera system arranged on the vehicle, at least one image of the charging unit as the vehicle approaches the charging unit and before the vehicle reaches a charging position of the charging operation; and
digitally processing the obtained at least one image of the charging unit in order to determine whether a foreign body is located on the charging unit.

14. The method according to claim 13, further comprising the acts of:
generating, via the camera system, a detection signal when a foreign body is identified on the charging unit;
transmitting the detection signal from the camera system of the vehicle to a charging control device outside of the vehicle; and
interrupting or reducing the electrical power being transmitted, via the charging control device, when the detection signal is received.

15. The method according to claim 14, further comprising the act of outputting a warning signal via the charging control device when the detection signal is received.

16. The method according to claim 13, further comprising the act of outputting a warning signal to a driver inside the vehicle upon identifying a foreign body located on the charging unit.

17. The method according to claim 13, further comprising the acts of:
storing, in the camera system, a reference image of the charging unit without a foreign body located on the charging unit;
comparing, via the camera system, the at least one obtained image with the reference image; and
determining the existence of a foreign body based on a deviation of the obtained image from the referenced image.

18. The method according to claim 17, wherein the camera system performs the comparison using a segmenting method or a pattern recognition method.

19. The method according to claim 17, wherein obtaining, via the camera system arranged on the vehicle, at least one image of the charging unit further comprises obtaining, via the camera system, at least one image of the charging unit when the vehicle is in the charging position at a beginning of the charging operation.

20. The method according to claim 19, wherein obtaining, via the camera system arranged on the vehicle, at least one image of the charging unit further comprises obtaining, via the camera system, at least one image of the charging unit when the vehicle is in the charging position during the charging operation.

* * * * *